United States Patent [19]

Hettche et al.

[11] Patent Number: 5,415,853

[45] Date of Patent: May 16, 1995

[54] COMPRESSED GAS PACKAGES USING POLYOXYETHYLENE GLYCERYL OLEATES

[75] Inventors: Helmut Hettche, Dietzenbach; Jurgen Engel, Alzenau; Reinhard Muckenschnabel, Frankfurt, all of Germany

[73] Assignee: Asta Medica Aktiengesellschaft, Dresden, Germany

[21] Appl. No.: 33,789

[22] Filed: Mar. 17, 1993

[30] Foreign Application Priority Data

Mar. 17, 1992 [DE] Germany .......... 42 08 505.5
May 8, 1992 [DE] Germany .......... 42 15 188.0
Sep. 16, 1992 [DE] Germany .......... 42 30 876.3

[51] Int. Cl.⁶ .................................. A61L 9/04
[52] U.S. Cl. ........................ 424/45; 424/46; 424/47
[58] Field of Search ............... 424/45, 46, 47

[56] References Cited

U.S. PATENT DOCUMENTS

| | | | |
|---|---|---|---|
| 4,010,252 | 3/1977 | Hewitt | 424/47 |
| 4,071,623 | 1/1978 | Van der Vies | 424/238 |
| 4,581,225 | 4/1986 | Su et al. | 424/45 |
| 4,863,720 | 9/1989 | Burghart et al. | 424/45 |
| 5,225,183 | 7/1993 | Purewal et al. | 424/46 |

FOREIGN PATENT DOCUMENTS

| | | |
|---|---|---|
| 0372777 | 11/1989 | European Pat. Off. . |
| 0499344 | 11/1989 | European Pat. Off. . |
| 0423695 | 10/1990 | European Pat. Off. . |

*Primary Examiner*—Thurman K. Page
*Assistant Examiner*—William E. Benston, Jr.
*Attorney, Agent, or Firm*—Cushman Darby & Cushman

[57] ABSTRACT

Aerosol compressed gas packages containing a member of the group consisting of polyoxyethylene-25-glyceryl trioleate, polyoxyethylene-30-glyceryl monooleate and polyoxyethylene-20-glyceryl monooleate as suspension stabilizer and/or valve lubricant. These materials are especially useful when the package contains TG 227 or TG 134a as the propellant.

6 Claims, No Drawings

COMPRESSED GAS PACKAGES USING POLYOXYETHYLENE GLYCERYL OLEATES

The present invention relates to aerosol containers for administering medication.

BACKGROUND OF THE INVENTION

Aerosol compressed gas packages have been used for many years for the most varied purposes. Aerosol compressed gas packages are understood to mean pressure-proof containers from which a mixture of liquefied propellant gas and active substance under pressure is released by operating a valve. Compressed gas packages are, for example, described in Sucker, Fuchs and Speiser (publishers), Pharmazeutische Technologie, Thieme, Stuttgart, 1991, p. 673–688. Aerosols and compressed gas packages are also described in List, Arzneiformenlehre, Wissenschaftliche Verlagsgesellschaft, Stuttgart, 1985, p. 8–18 and in Voigt, Lehrbuch der pharmazeutischen Technologie, VCh, Weinheim, 1987 on pages 427–436. This popular dosage form is also extensively described by Thoma, Aerosole, published by the author, Frankfurt am Main, 1979. In the medical sector they are advantageously used when active substances have to be directly transported to the lungs and deposited there. The advantage of aerosol compressed gas packages lies in the fact that their use produces a cloud of finely dispersed particles which can be inspired by the patient. The result is a rapid onset of action at the site of action—the lung—which is, for example, of critical importance in bronchial asthma therapy. On the other hand, local application of this nature directly into the lung can keep the dosage low in the prevention of asthma attacks using prophylactically acting substances. This minimizes the appearance of undesirable side effects compared to application via the gastro-intestinal tract.

Aerosol compressed gas packages have therefore found wide use in the treatment of respiratory tract disorders. They are simply, safe and economically priced. Possible problems in coordinating the inspiration of the patient and triggering of an aerosol burst can be avoided either by expansion chambers (spacers) interposed between the aerosol packaging and the mouth of the patient, or by special constructions of the inhalers in which the inspiration of the patient triggers the aerosol burst.

Apart from use in bronchial asthma prophylaxis and in the treatment of acute asthma attacks, the formulation of the invention can also find use as a nasal spray and for application as a mouth spray (lingual and buccal application).

CFCs (fluorinated chlorinated hydrocarbons) have hitherto been used as propellants for dosage aerosols. The following fluorinated chlorinated hydrocarbons and hydrocarbons can, for example, be used as propellants: pentane, n-butane, iso-butane, TG 11, TG 12, TG 21, TG 22, TG 23, TG 113, TG 114, TG 115, TG 142b and TG C 318.

The type designation of the fluorinated chlorinated hydrocarbons is derived from the following code system: Number in unit place=number of fluorine atoms (F) Number in tens place minus 1=number of hydrogen atoms (H) Number in hundreds place plus 1=number of carbon atoms (C) Number of free valencies=number of chlorine atoms (Cl)

Since the postulation of the "ozone theory" (breakdown of the ozone in the stratosphere because of CFCs and other organic compounds containing chlorine) there has been a search for liquid gases which can serve as propellants and which are neither combustible, nor liable to break down ozone and which are, moreover, not harmful to health.

For some time, non-chlorinated fluorohydrocarbons such as 1,1,1,2-tetrafluoroethane (TG 134a) or 2H-heptafluoropropane (TG 227) have been used.

Apart from TG 134a and TG 227, mention may also be made of TG 152a (difluoroethane, $CH_3CHF_2$), TG 143a (trifluoroethane, $CH_3CF_3$) and TG 161 (fluoroethane, $CH_3CH_2F$).

However, it is a disadvantage of these propellants that the suspension stabilizers and valve lubricants, needed for their use, are not sufficiently soluble in them. Thus the use of TG 134a requires about 25% ethanol in order to dissolve the sorbitan trioleate (Span ®85) hitherto used in aerosol suspensions to an adequate extent (see Published European Patent Application EP 372 777 A 2). It is, for example, also possible to use the following compounds: multivalent alcohols such as glycerol, esters such as ethyl acetate, ketones such as acetone and hydrocarbons such as hexane and heptane, pentane and also isopropanol. A disadvantage of such high concentrations is that the active substance present in the suspension may tend to dissolve, resulting in a risk of particle growth. If the active substance particles grow during storage of a suspension of this type above a size of 10 μm there may be blockage of the aerosol valve. In addition, there may be a reduction in effectiveness of the aerosol, since the active substance particles can no longer reach the deeper parts of the lungs because of their size.

There is consequently an urgent need for substances which
- are physiologically acceptable
- are technologically suitable to stabilize aerosol suspensions of TG 134a or TG 227 and to improve the function of the dosage valve
- are soluble in TG 134a or TG 227 without, or using the smallest amounts of, other physiologically acceptable solubilizers
- have an acceptable taste.

SUMMARY OF THE INVENTION

It has now surprisingly been found that polyoxyethylene-25-glyceryl trioleate constitutes a substance with the above-mentioned requisite properties (trade name "Tagat ®TO" manufacturer: Goldschmidt, Essen). Polyoxyethylene-25-glyceryl trioleate has the following structural formula:

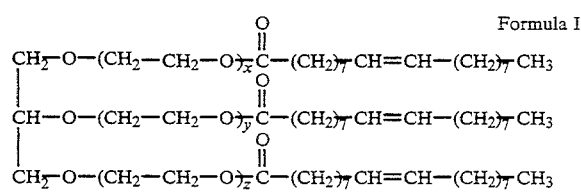

Formula I where: $x+y+z=20-30$

The HLB value is 11.3; the hydroxyl number is between 18 klllllllllllllllllllland 33; the maximum value of the acid number is 2; the saponification number is between 75 and 90 and the iodine number between 34 and 40.

The hydroxyl number was determined according to DGF-C-V 17*a*, the acid number according to DGF-C-V 2, the saponification number according to DGF-C-V 3 and the iodine number according to DGF-C-V 11. Polyoxylethylene-25-glyceryl trioleate is an amber-colored liquid. Polyoxylethylene glyceryl trioleate is

- physiologically acceptable (comparable to sorbitan trioleate (=Span ®85))
- technologically suited to stabilize aerosol suspensions of TG 134a and/or TG 227 and to improve the function of the dosage valve
- soluble in TG 134a or TG 227 in the presence of less than 1–2% ethanol or comparable alcohols
- acceptable in taste Other compounds suitable as suspension stabilizers which display the above-mentioned properties are:

Tagat ®O

In chemical terms, Tagat ®O is a polyoxyethylene-30-glyceryl monooleate.

Polyoxyethylene-30-glyceryl monooleate has the following structural formula:

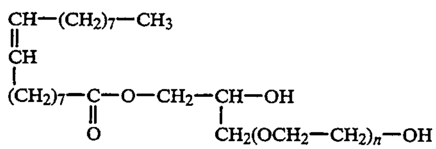

Formula II where n: about 30.

The HLB value is 16.4; the hydroxyl number is between 50 and 65; the maximum value of the acid number is 2; the saponification number is between 30 and 45 and the iodine number between 15 and 19.

Tagat ®O2

In chemical terms, Tagat ®O2 is a polyoxyethylene-20-glyceryl monooleate.

Polyoxyethylene-20-glyceryl monooleate has the following structural formula:

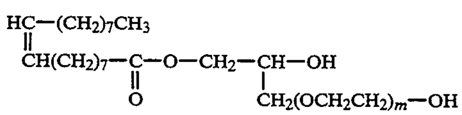

Formula III where m is about 20.

The HLB value is 15.0; the hydroxyl number is between 70 and 85; the maximum value of the acid number is 2; the saponification number is between 40 and 55 and the iodine number between 21 and 27.

The dissolving power of a mixture of TG 134a or TG 227 with 1–2% ethanol for the conventional active substances is so low that it has no effect on possible crystal growth of the active substances. The suspension stabilizers hitherto used in commercial preparations had an HLB value of less than 5 (e.g. Span 85: HLB=1.8) and thus lie in the range of the water/oil emulsifiers. (Voigt, Lehrbuch der pharmazeutischen Technologie, Weinheim, 1987, p. 332). It is therefore surprising that a substance such as polyoxyethylene-25-glyceryl trioleate, polyoxyethylene-30-glyceryl monooleate, and polyoxyethylene-20-glyceryl monooleate which have HLB values of 11.3 to 16.4 is suitable for this purpose. The amount of polyoxyethylene-25-glyceryl trioleate, polyoxyethylene-30-glyceryl monooleate, and polyoxyethylene-20-glyceryl monooleate which are used, relative to the amount of active substance used is, for example, between 0.3 and 8000, in particular 5 and 4000 and, particularly preferred, between 15 and 2500 weight %. The following may be used as active substances:

Analgesics, anti-allergics, antibiotics, anticholinergics, antihistamines, anti-inflammatory substances, antitussives, bronchodilatants, diuretics, enzymes, cardiovascularly acting substances, hormones, proteins and peptides. Examples of analgesics are codeine, diamorphine, dihydromorphine, ergotamine, fentanyl, morphine; examples of anti-allergics are cromoglycic acid, nedocromil; examples of antibiotics are cephalosporines, fusafungine, neomycine, penicillins, pentamidine, streptomycine, sulfonamides, tetracyclines; examples of anticholinergics are atropine, atropine methonitrate, ipratroprium bromide, oxitropium bromide, trospium chloride; examples of antihistamines are azelastine, flezelastine, methapyrilene; examples of anti-inflammatory substances are beclomethasone, budesonide, dexamethasone, flunisolide, fluticason, tipredane, triamcinolone; examples of antitussives are narcotine, noscapine; examples of bronchodilators are bambuterol, bitolterol, carbuterol, clenbuterol, ephedrine, epinephrine formoterol, fenoterol, hexoprenaline, ibuterol, isoprenaline, isoproterenol, metaproterenol, orciprenaline, phenylephrine, phenylpropanolamine, pirbuterol, procaterol, reproterol, rimiterol, salbutamol, salmeterol, sulfonterol, terbutaline, tolobuterol; examples of diuretics are amiloride, furosemidein; an example of enzyme is trypsin; examples for cardiovascular substances are diltiazem and nitroglycerine; examples of hormones are cortisone, hydrocortisone, prednisolone; examples of proteins and peptides are cyclosporines, cetrorelix, glucagon, insulin. Other active substances that can be used are adrenochrome, colchicine, heparin, scopolamine.

It is also possible to use combinations of the above-listed substances.

The active ingredients listed by way of example may be used as free bases or acids or as pharmaceutically acceptable salts. It is, for example, possible to use physiologically acceptable alkaline earth metals or alkali metals or amines as well as for example acetate, benzene sulfonate, benzoate, hydrogen carbonate, hydrogen tartrate, bromide, chloride, iodide, carbonate, citrate, fumarate, malate, maleate, gloconate, lactate, pamonate, hydroxynaphthoate and sulphate as counterions. Esters may also be used, for example acetate, acetonide, propionate, dipropionate, valerate. The amount of Tagat ®TO, Tagat ®O or Tagat ®O2 relative to the mixture, composed of active substances, propellant gas or propellant gas mixtures, optionally auxiliary substances, is, for example, 0.01% by weight to 5% by weight, in particular 0.2% by weight to 2.5% by weight, and particularly preferred 0.75% by weight to 1.5% by weight.

Co-solvents may be added, for example aliphatic alcohols having 2 to 6 carbon atoms or their esters or ketones or polyols. Examples are ethanol, isopropanol, propylene glycol, acetone, acetic acid ethyl ester, n-propanol, preferably ethanol and isopropanol.

The amount of ethanol or isopropanol, relative to the total mixture, is 0% by weight to 10% by weight, in particular 0.1% by weight to 2% by weight and, particularly preferred, 0.2% by weight to 1% by weight.

It is, of course, also possible to add other substances that are active at the interface, such as, for example, listed in EP 0 372 777.

The active substances can either be suspended at normal air pressure, in which case the suspension medium must be cooled to low temperatures (for example −35° C. to −55° C.) or within a pressure vessel, where the operation can be carried out at normal temperatures (room temperature 15° to 25° C. The suspension is homogenized and then dispensed into pressure cans which are closed with a dosage valve or subsequently closed.

DETAILED DESCRIPTION OF PREFERRED EMBODIMENTS

The following examples illustrate the invention.

EXAMPLE 1

1000 g 2H-heptafluoropropane (=propellant 227) are cooled to a temperature of about −55° C. and reacted with stirring with a solution of 11.7 g polyoxyethylene-25glyceryl trioleate (trade name: Tagat®TO, Goldschmidt AG) in 11.7 g absolute ethanol. 16.8 g micronized cromoglycic acid, disodium salt and 8.4 g micronized reproterol hydrochloride as well as 0.9 g micronized saccharine-sodium and 6.75 g peppermint oil are then added, and the resultant suspension is intensively homogenized. With further stirring and cooling the suspension is made up to 1170.0 g with cooled propellant 227 and then filled into metal cans which are closed with dosage valves that release 50 µl of the suspension per stroke. Each stroke releases 1 mg cromoglycic acid, disodium salt and 0.5 mg reproterol hydrochloride.

EXAMPLE 2

1000 g 2H-heptafluoropropane (=propellant 227) are cooled to a temperature of about −55° C. and reacted with stirring with a solution of 11.7 g polyoxyethylene-30glyceryl monooleate (trade name: Tagat®O, Goldschmidt AG) in 11.7 g absolute ethanol. 16.8 g micronized cromoglycic acid, disodium salt and 8.4 g micronized reproterol hydrochloride as well as 0.9 g micronized saccharine-sodium and 6.75 g peppermint oil are then added and the resultant suspension is intensively homogenized. With further stirring and cooling the suspension is made up to 1170.0 g with cooled propellant 227 and then filled into metal cans which are closed with dosage valves that release 50 µl of the suspension per stroke. Each stroke releases 1 mg cromoglycic acid, disodium salt and 0.5 mg reproterol hydrochloride.

EXAMPLE 3

1000 g 2H-heptafluoropropane (=propellant 227) are cooled to a temperature of about −55° C. and reacted with stirring with a solution of 11.7 g polyoxyethylene-20-glyceryl monooleate (trade name: Tagat®O2, Goldschmidt AG) in 11.7 g absolute ethanol. 16.8 g micronized cromoglycic acid, disodium salt and 8.4 g micronized reproterol hydrochloride as well as 0.9 g micronized saccharine-sodium and 6.75 g peppermint oil are then added and the resultant suspension is intensively homogenized. With further stirring and cooling the suspension is made up to 1170.0 g with cooled propellant 227 and then dispensed into metal cans which are closed with dosage valves that release 50 µl of the suspension per stroke. Each stroke releases 1 mg cromoglycic acid, disodium salt and 0.5 mg reproterol hydrochloride.

EXAMPLE 4

The operation is carried out as in Example 1, except that 16.8 g micronized D-18024 are used instead of 16.8 g micronized cromoglycic acid, disodium salt and 8.4 g micronized reproterol hydrochloride. Each stroke releases 1 mg D-18024. D-18024 has the following structural formula.

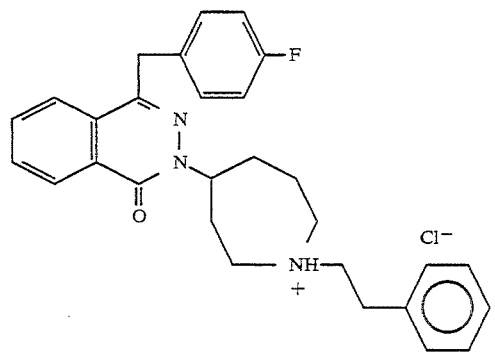

The INN of D-18024 is flezelastine hydrochloride.

EXAMPLE 5

The operation is carried out as Example 1 except that 4.2 g micronized budesonide are used instead of 16.8 g micronized cromoglycic acid, disodium salt, 8.4 g micronized reproterol hydrochloride, 0.9 g micronized saccharine-sodium and 6.75 g peppermint oil. One stroke contains 0.25 mg budesonide.

EXAMPLE 6

1000 g heptafluoropropane (=propellant 227) are cooled to a temperature of about −55° C. and reacted with stirring with a mixture of 11.7 g polyoxyethylene-25-glyceryl trioleate (trade name: Tagat®TO, Goldschmidt AG) and 6.75 g Dentomint PH 799 959 (manufacturer: Haarmann und Reimer, Holzminden). With further stirring and cooling, 16.8 g micronized cromoglycic acid, disodium salt and 8.4 g micronized reproterol hydrochloride as well as 0.9 g micronized saccharine-sodium are added and the resultant suspension is intensively homogenized. With further stirring and cooling the suspension is made up to 1170.0 g with cooled propellant 227 and then filled into metal cans which are closed with dosage valves that release 50 ul of the suspension per stroke. Each stroke releases 1 mg cromoglycic acid, disodium salt and 0.5 mg reproterol hydrochloride.

What is claimed is:

1. In an aerosol compressed gas package for administering a biologically active substance, comprising an aerosol container a propellant in said container and a biologically active substance dispersed in said propellant;

the improvement in which said propellant also contains a member of the group consisting of polyoxyethylene-25glyceryl trioleate, polyoxyethylene-30-glyceryl monooleate and polyoxyethylene-20-glyceryl monooleate as suspension stabilizer and/or valve lubricant.

2. An aerosol compressed gas package as set forth in claim 1 in which the suspension stabilizer is polyoxyethylene-25-glyceryl trioleate.

3. An aerosol compressed gas package as set forth in any one of claim 1 in which the proportion of said suspension stabilizer relative to the total weight of the contents of said container is between 0.01 and 5 weight %.

4. An aerosol compressed gas package as set forth in claim 3 in which the proportion of said suspension stabilizer relative to the total weight of the contents of said container is between 0.2 and 2.5 weight %.

5. An aerosol compressed gas package as set forth in claim 3 in which the proportion of said suspension stabilizer relative to the total weight of the contents of said container is between 0.75 and 1.5 weight %.

6. An aerosol compressed gas packages according any one of claim 1 in which the propellant is at least one member of the group consisting of TG 227 and TG 134a.

* * * * *